United States Patent
Ollivier

(10) Patent No.: US 9,849,280 B2
(45) Date of Patent: Dec. 26, 2017

(54) CORONARY VENOUS PACING LEAD AND ANCHORING SCREW SYSTEM

(75) Inventor: Jean Francois Ollivier, Villiers le Bacle (FR)

(73) Assignee: SORIN CRM SAS, Clamart (FR)

( * ) Notice: Subject to any disclaimer, the term of this patent is extended or adjusted under 35 U.S.C. 154(b) by 793 days.

(21) Appl. No.: 12/834,385

(22) Filed: Jul. 12, 2010

(65) Prior Publication Data
US 2011/0015715 A1 Jan. 20, 2011

(30) Foreign Application Priority Data

Jul. 15, 2009 (FR) .................. 09 54873

(51) Int. Cl.
*A61N 1/00* (2006.01)
*A61N 1/05* (2006.01)
*A61M 25/00* (2006.01)

(52) U.S. Cl.
CPC .......... *A61N 1/056* (2013.01); *A61M 25/0041* (2013.01); *A61N 1/0573* (2013.01); *A61N 2001/0585* (2013.01)

(58) Field of Classification Search
CPC .................. A61N 1/056; A61N 1/0573; A61N 2001/0585; A61M 25/0041
USPC .................. 600/585; 607/122, 125, 119, 127
See application file for complete search history.

(56) References Cited

U.S. PATENT DOCUMENTS

| 4,716,757 A | 1/1988 | Mcgregor et al. |
|---|---|---|
| 4,867,174 A | 9/1989 | Skribiski |
| 4,925,445 A | 5/1990 | Sakamoto et al. |
| 5,476,500 A | 12/1995 | Fain et al. |
| 5,640,955 A | 6/1997 | Ockuly et al. |
| 5,658,327 A * | 8/1997 | Altman et al. ............... 607/127 |
| 5,728,148 A | 3/1998 | Bostrom et al. |
| 5,807,324 A | 9/1998 | Griffin, III |
| 5,807,339 A | 9/1998 | Bostrom et al. |

(Continued)

FOREIGN PATENT DOCUMENTS

| EP | 0 778 044 | 12/1995 |
|---|---|---|
| EP | 0993840 | 4/2000 |

(Continued)

OTHER PUBLICATIONS

Foreign Search Report (Annexe Au Rapport De Recherche Preliminaire; Ralatif A La Demande De Brevet Francais No. FR 0954873 FA 724289), Jan. 21, 2009.

(Continued)

*Primary Examiner* — Mallika D Fairchild
(74) *Attorney, Agent, or Firm* — Foley & Lardner LLP

(57) ABSTRACT

A system implantable in the coronary venous system, including a pacing lead with an anchoring screw is disclosed. The system includes a stimulation lead (10) for stimulating a left heart cavity of a patient, and a removable catheter (26) for implanting the lead. The lead (10) has at least one stimulation electrode having an anchoring screw (14) that penetrates into the epicardial tissue of the patient. The catheter tube (26) is a pre-shaped tube with two curvatures in the absence of stress. The two curvatures are inscribed in two separate surfaces (38, 40) for self-orientating the distal end of the catheter tube into the target vein and maintaining the axis of the anchoring screw towards the epicardial wall during the screwing of the lead head.

20 Claims, 2 Drawing Sheets

(56) References Cited

U.S. PATENT DOCUMENTS

| | | | |
|---|---|---|---|
| 5,837,007 | A | 11/1998 | Altman et al. |
| 5,868,700 | A * | 2/1999 | Voda .............................. 604/510 |
| 5,897,584 | A | 4/1999 | Herman |
| 6,385,492 | B1 * | 5/2002 | Ollivier et al. ............... 607/122 |
| 6,408,214 | B1 * | 6/2002 | Williams et al. ............. 607/122 |
| 6,944,506 | B1 | 9/2005 | Morgan et al. |
| 7,201,724 | B2 | 4/2007 | Jarl et al. |
| 7,462,184 | B2 * | 12/2008 | Worley et al. ................ 606/129 |
| 2002/0169377 | A1 | 11/2002 | Khairkhahan et al. |
| 2002/0193811 | A1 | 12/2002 | Chan |
| 2003/0208220 | A1 | 11/2003 | Worley et al. |
| 2006/0122682 | A1 | 6/2006 | Somer et al. |
| 2009/0071012 | A1 | 3/2009 | Shan et al. |

FOREIGN PATENT DOCUMENTS

| | | |
|---|---|---|
| EP | 1 920 795 | 5/2008 |
| EP | 2039390 | 3/2009 |
| WO | WO 91/15152 | 10/1991 |
| WO | WO 94/20165 | 9/1994 |
| WO | WO 02/04062 | 1/2002 |
| WO | WO 2005/082445 | 9/2005 |

OTHER PUBLICATIONS

European Search Report dated Aug. 20, 2013 received in European Application No. 10 16 7037.0.

\* cited by examiner

CORONARY VENOUS PACING LEAD AND ANCHORING SCREW SYSTEM

FIELD

The present invention relates to "active implantable medical devices" as defined by the Jun. 20, 1990 Directive 90/385/EEC of the European Communities, particularly to implantable devices that continuously monitor a patient's heart rhythm and, if necessary, deliver at the patient's heart electrical pulses for stimulation or resynchronization, and more particularly to cardiac pacing leads implanted in the coronary network of the patient's heart to allow pacing of a left (ventricle or atrium) cavity.

BACKGROUND

Unlike the right cavities of the heart, for which it is sufficient to implant endocardial leads via the right peripheral venous network, the implantation of permanent leads into a left heart cavity involves significant operating risks, e.g., passing bubbles to the cerebral vascular network located downstream of the left ventricle. For this reason, when it is desirable to stimulate the left cavity, a stimulation catheter is introduced via the coronary network, rather than in the cavity. The lead is equipped with an electrode to be applied against the wall of the epicardium and to steer it toward the left ventricle or left atrium, as appropriate.

The introduction of such a lead is made through the coronary sinus opening into the right atrium, thus by an endocardial approach. It is then guided and driven along the network of coronary veins to the chosen stimulation site. This intervention is particularly difficult given the peculiarities of the venous system and of its access paths, particularly because of the valves and tortuosities, and because of the gradual reduction in diameter of the vessel as the lead progresses in the selected coronary vein. Furthermore, the position of the stimulation site, a good electrical contact of the electrode with the tissue of the epicardium, and the correct orientation of the stimulating electrode, are particularly important aspects to consider when implanting the lead into the heart cavity.

For example, in the case of a "multisite" pacemaker, preferably for the interventricular resynchronization, the two points of stimulation of the left ventricle/right ventricle should be as far apart as possible, so as to optimize the resynchronization of all the cardiac chambers. It is also important to reduce the risk of phrenic nerve stimulation during or after implantation.

These aspects must be evaluated not only at the time of implantation, but it is also necessary that the quality and accuracy of the contact in the site of stimulation are not significantly changed in the medium term, for example, because of patient movements such as changes in posture, wide movements of arms and heavy breathing.

EP 0993840 A1 and its US counterpart U.S. Pat. No. 6,385,492 (ELA Medical, now known as Sorin CRM S.A.S) describe a pre-shaped lead adapted for implantation in the coronary venous system. The lead head includes a sector electrode and has a double curvature to ensure a self-orientation of the lead tip so that the sector electrode is directed toward the epicardium when the lead head has reached its final position. This pre-shaped lead is used in combination with a stylet that allows the operator to more or less reform the curvature during implantation to facilitate the progression of the lead head to the heart in the peripheral venous system, then the search of the coronary sinus, and finally, the progression of the lead head in the coronary system to the selected site of stimulation. A commercial embodiment of this type of lead is marketed by Sorin CRM under the Situs LV lead brand.

The pre-shaped leads are sometimes difficult to advance, as they move along according to the principle of least energy. At an applied force to insert the lead or torque to rotate the lead, the lead moves or rotates in the direction and orientation where the least energy is required. In addition, their extraction capacity remains unknown, with a risk of damaging the coronary network veins during explantation of the lead.

Finally, one of the classical drawbacks of conventional pre-shaped leads is their tendency to restore to their original shape (due to the principle of least energy), which causes postoperative micro-displacements affecting the quality of the thresholds and/or the resynchronization.

Another problem is the difficulty in finding a good stimulation site, to achieve a good electrical contact of the electrode against the tissue of the epicardium, and maintain this contact despite variations or various solicitations in time. It is also essential to avoid any phrenic stimulation, both during and after the implantation.

To overcome these difficulties, it was proposed to have multiple electrodes along the lead body to increase the chances of an acceptable compromise, possibly by giving the lead body a particular lead conformation. The operator can thus choose, among the various electrodes present on the lead body, the one providing the best electrical efficiency. On the other hand, to reduce risks of variation in the medium term of the electrical contact and of later phrenic stimulation, manufacturers have introduced the concept of "electronic repositioning" to direct or redirect the electric field between different electrodes placed along the stimulation lead of the left ventricle and/or with one of the electrodes of the stimulation lead from the right ventricle, in order to avoid a re-intervention. The counterpart of this solution is a growing complexity of the structure of the lead, an increase in the number of electrodes causing an increase in the number of components and electrical wiring, or the use of multiplexing circuits for selecting from among the various electrodes on the same lead.

The WO-A-02/04062 A2 (Medtronic) describes a technique of "telescopic approach" usually used in various applications (notably in angioplasty) to make a cannulation either of the ostium of the coronary sinus or a lateral vein. This technique is based on the use of two catheters, one inserted inside the other, with longitudinal and circular relative movements possible, the movements being controlled by the physician on the proximal side. It is theoretically possible to orient the termination of the inner catheter to direct the termination of its distal curve to the epicardium but, as in the targeted application the catheter is "partitioned/adjusted" in the venous network, the expected equilibrium position generates a lot of counter torque that must be opposed. As a result, the expected equilibrium position is relatively unstable.

Several phenomena complicate the task of the physician, for example, the fact that the fine control of the orientation is subject to the quality of the torque transmission, which is particularly linked to: (i) the diameter of the catheter, which is expected to be as small as possible and (ii) the length of the catheter, which is in the order of 70 cm. The small diameter and long length of the catheter are unfavorable for good control. This fine control is also perturbed by the cardiac movements which render the equilibrium of the system unstable, as the screwing operation can occur over a duration in the order of ten seconds. Keeping the catheter in place while performing the screwing operation may require two operators.

The implantation of a catheter is consequently "operator dependent" because it is difficult to obtain a secured positioning of the anchoring helical screw of the catheter.

The anchoring helical screw needs to be oriented in an appropriate direction during screwing. Indeed, the fixation qualities of a screw lead are broadly known in the field of cardiac pacing leads, but this technique is not used as of today in the coronary sinus because the risks of dissection of the coronary sinus is too high. Nevertheless, the fixation remains the main problem when implanting the left ventricular pacing leads via the coronary sinus.

The U.S. Pat. No. 5,837,007 (Pacesetter) proposes a solution to this problem by means of a retractable screw. But this technique is complex, because it requires at least three components (up to six components) with the use of a soluble element or a component having mechanical characteristics that significantly change after impregnation by corporeal fluids. Furthermore, the torque transmission is performed via a stylet that directly engages the screw. This requires an additional accessory and complicates the operation, which is already complex and delicate to implement.

The present invention aims to remedy the above difficulties, in particular by overcoming problems associated with the use of leads equipped with multiple electrodes.

SUMMARY

It is therefore an object of the present invention to enable an accurate choice and screening of a stimulation site, and to ensure an optimum and durable stability of the electrode placement on the stimulation site.

If the electrode can be fixed in place at the stimulation site where it was originally placed, subsequent movements of the lead after the fixation are of no concern thus it would be unnecessary to overcome the consequences of such movements by sophisticated techniques such as electronic repositioning or the selection among multiple electrodes.

The present invention proposes to use as the stimulation lead for the left ventricle a screw anchor similar to the technique for attaching stimulation leads in the right cavities.

The screw anchor stimulation leads for the right cavities are endocardial leads that are introduced to the apex of the right ventricle. The lead tip is pushed to the bottom of the cavity (ventricular apex) where it abuts, and the physician assumes that the correct permanent position of the lead is reached. The lead head is rotated and screwed into the tissue of the myocardium in a reversible manner. When the lead needs to be removed or relocated, the physician can unscrew the lead and redo the fixation operation.

The direct implantation of such a lead in the coronary system, however, presents several difficulties. Firstly, the handling of a fixed or retractable screw lead into the sinus would create high risks, with damage levels varying up to the complete dissection of the coronary sinus. On the other hand, once the lead head is positioned at the stimulation site, the screw tends to be oriented in a direction parallel to the general orientation of the vein, not in the direction of the epicardial wall, despite the electrode must precisely be in close contact with the tissue of the epicardium for fixation.

To solve both of these problems (safe access to the desired site and orientation of the lead head to the epicardium), the present invention combines the lead with a screw setting tool specifically ensuring optimum safety and providing an adapted angle of screwing.

In one embodiment of the present invention, the screw setting tool is a preformed guide catheter with a double curve similar to that described for a lead in the aforementioned EP 0993840 A1 and its US counterpart U.S. Pat. No. 6,385,492. The bi-curve shape is applied to the lead itself, because it has a sector electrode. Means for keeping the lead against the wall of the vein at the stimulation site is provided to ensure that the electrode is directed toward the epicardium.

In one embodiment of the present invention, the bi-curve shape is applied to the setting tool to the guide catheter alone. The sector lead is replaced with an anchoring screw lead with all the inherent advantages of this type of lead, including the reduction or complete elimination of the risk of displacement after fixation, the excellent electrical performance in contact with a myocardial tissue, and the ease of extraction.

The present invention uses the local anatomical configuration of the coronary sinus and its tributaries (a left turn) to self-orient and stabilize the distal end of the catheter. The local self-orientation provides a sufficient torque to orient the support curvature in the desired position, allowing a precise positioning of the screw head at the time to start screwing into the tissue. This technique is not operator-dependent, and the operator has only to push the catheter into the target vein to self-orient after several beats in the desired position, freeing his hands from the screwing operation.

More specifically, the present invention is directed to an implantable system of the general type notably described in WO 02/04062 A2 cited above, more particularly to an implantable system implanted in the coronary venous system including a pacing lead and a removable catheter for the implantation of the pacing lead. The pacing lead includes: a lead body with a sheath in a deformable material; at the distal end, a lead head with at least one stimulation electrode coming into contact with a region facing the epicardium of the wall of a targeted vein of the coronary network, and on the proximal side, means of coupling to a generator of an active implantable medical device. The catheter includes a hollow tube open at both ends with a lumen. The lead is inserted within the catheter lumen and moved in translation inside the catheter, first to a retracted position where the lead head is positioned at the distal end of the catheter lumen, for example, flush with the distal end, or recessed relative to the catheter lumen distal end, and is then moved to a deployed position where the lead head with the electrode emerges from and extends beyond the opening of the hollow tube. The hollow tube of the catheter is elastically deformable and relatively more rigid than the sheath of the lead body.

In accordance with one embodiment of the present invention, the lead is a screw lead that is equipped with a projecting anchoring helical screw axially extending from the lead head, and penetrates the tissue of the epicardium under the action of a screw motion imparted to the lead head. The sheath of the lead body preferably is not pre-shaped at its distal end. The catheter includes a single tube that is pre-shaped having, in the absence of any stress, two curves in two separate respective planes, said two curves auto-orienting the distal catheter tube into the target vein with the lead head in the retracted position, and maintaining the axis of the anchoring screw towards the epicardium during a combined movement of screwing and moving of the lead head towards the extended position.

In accordance with one embodiment, the two distinct surfaces defining the respective two curves have a first surface corresponding to a curvature of an orientation curve defined by a pre-shaping of the catheter tube and a second surface corresponding to a curvature defined by a natural curve of the distal end of the catheter tube.

In one embodiment, the anchoring screw is a screw extending axially of the lead head. In another embodiment, the anchoring screw is a retractable mobile screw into a housing of the lead head. The anchoring screw may be an active screw forming said stimulation electrode, or a passive screw, electrically decoupled from said stimulation electrode.

The sheath of the lead body has sufficient rigidity in torsion to transmit a rotating movement over its length from the proximal end of the lead to screw the anchoring screw. Alternatively, if the rigidity in torsion of the sheath of the lead body is insufficient to transmit a rotating movement over the length from the proximal end of the lead, a removable stylet is introduced in a lumen of the lead body, movable in translation within the lumen up to the lead head and including means of coupling in rotation with the lead head. The stylet has a sufficient rigidity in torsion to transmit a rotation movement over its length to the means of coupling from the proximal end of the stylet to screw the anchoring screw.

In a preferred embodiment the diameter of the lead body is less than or equal to 5 French (1.65 mm).

In one embodiment of the present invention, the anchoring screw includes a helical end portion adapted to penetrate the tissue of the epicardium and connect to the lead head by a transition portion mechanically deformable in flexion, more preferably a part of the helical screw with adjacent turns. More preferably, the anchoring screw includes an helix end portion penetrating the tissue of the epicardium and including an active region of an electrically conductive tip extending through an electrically insulated part, with an axial length of the active region of electrically conductive tip that is less or equal to 1 mm.

In yet another embodiment, the system includes a removable guide wire. The removable guide wire, after having been introduced into the coronary venous system to the target vein, receives the catheter and allows by sliding the guiding of the catheter to this target vein.

The catheter with pre-shaped tube is preferably a sub-catheter for vein selection. The system also includes a main catheter including a hollow tube open at both ends with a lumen within which the catheter is inserted and moved in translation and rotation within the catheter to advance into the main venous system until it reaches the coronary target vein.

BRIEF DESCRIPTION OF THE DRAWINGS

Further features, advantages and characteristics of the present invention will become apparent to a person of ordinary skill in the art in view of the following detailed description of preferred embodiments of the invention, made with reference to the drawings annexed, in which like reference characters refer to like elements, and in which.

DETAILED DESCRIPTION

Figure 1:
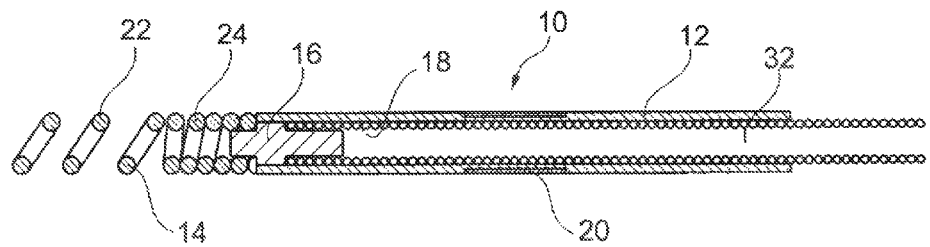
FIG. 1 is a sectional view of the lead head of the system, according to the present invention.

Examples of an implementation of the present invention will now be described with reference to the drawings FIGS. 1-5. In the figures, reference 10 generally refers to the screw lead of the system according to the present invention. The lead 10 comprises a lead body 12 which structure is in itself known, usually a polyurethane sheath to reduce friction when the catheter is inserted into a guide catheter, and to provide better sensitivity and better transmission of torque torsion. The diameter of the sheath of the lead body 12 is chosen to be thin enough to be compatible with the sub-selection catheters of veins of the coronary network, typically less than or equal to 5 French (1.65 mm).

The lead 10 is terminated at its distal end by a helical anchoring screw 14 made of a conductive material, connected through a metal tip 16 to an inner conductor 18 such as a spiral conductor providing electrical continuity between the anchoring screw 14 that is an electrode for collection and stimulation and a generator located at the proximal end (not shown) of the lead 10. It should be understood that lead body 12 made of a polyurethane sheath provides rigidity in torsion to transmit torque from the proximal end to the distal end and to rotate the screw 14 to make it penetrate into the heart tissue.

The conductive material of the screw is advantageously a NiTi alloy (nitinol), which has a capacity to transmit a sufficient torque for the intended application. The main advantage of this material is its extreme fatigue endurance. The disadvantage of nitinol is its relative high electrical resistance, but this drawback may be compensated by a bi-material structure comprising a silver core (for electrical conductivity) wrapped or coated by nitinol (for properties of resistance to mechanical stress) such that the less mechanically tough material (silver) is encapsulated in a sheath of nitinol.

For bipolar stimulation, the lead is also provided with a ring electrode 20 connected to the generator by a separate conductor (not shown) in a manner well known to persons of ordinary shell in the art.

The anchoring screw 14 is advantageously carried out with a distal portion 22 formed of non-touching turns over a length of about 1.5 to 2 mm. The distal portion 22 is connected to the lead body 12 via a mechanical transition portion 24 having flexibility in flexion, for example, a part formed by adjacent turns in the absence of stress of the screw.

The purpose of this transition portion 24 is to introduce between the screw 14 itself (the part that will penetrate into the tissues) and the lead body 12 an elastic function to limit the mechanical action of the distal part of the lead 10 on the cardiac tissues and/or the veins. Advantageously, this elastic feature (i) does not alter the torque transmission between the lead body 12 and the screw 14 under the two aspects of efficacy and safety (coring effect); (ii) does not alter the transmission of the electrical pulse, and (iii) is extremely resistant to flexion/compression events.

On the other hand, the screw 14 is advantageously insulated over its length, for example, by a coating of parylene, except on the last millimeter of the distal part, which is the only electrically active part of the screw 14. This structure reduces the stimulation surface and thereby reduces the risk of phrenic nerve stimulation. This electrically active part will also be buried deep into the wall of the epicardium, thereby concentrating the electric flow to the target tissue and stimulate a deep and more physiological zone.

A long screw (in the order of 10-15 mm) penetrates deeply into the ventricular wall and performs a localized endocardial stimulation ensuring during stimulation a faster wave of depolarization from the endocardium to the epicardium. To avoid the risk of coring, the internal lumen of the flexible portion of the screw 14 is equipped with a silicone cartridge (possibly filled with a steroid) to maximize the effect of abutment to the transmission of torque.

In the illustrated drawings, the screw 14 is an active screw playing (at least at its distal end) the role of a stimulation electrode.

Alternatively, the screw 14 is an electrically passive screw used for anchoring the lead 10 against the wall of the epicardium. The lead 10 may be provided at its end with a distal electrode in the shape of a ring electrode, a second electrode, or other suitable configurations.

Figure 2:
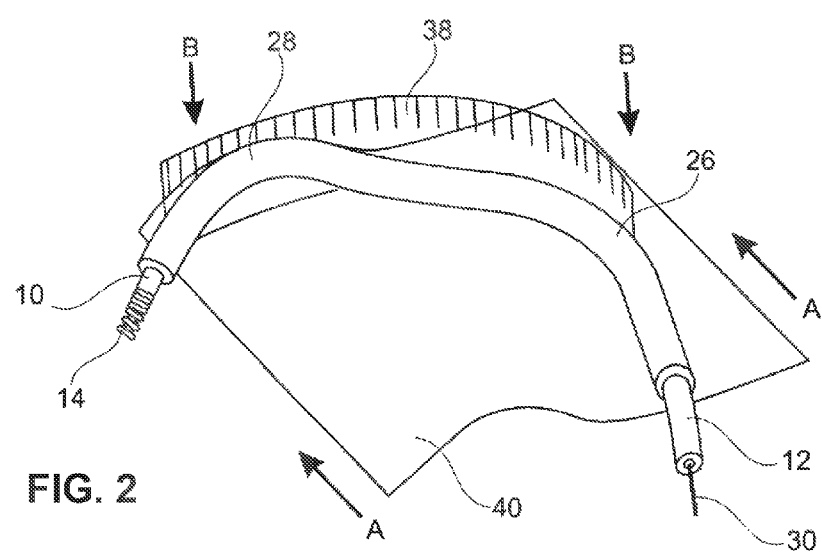
FIG. 2 schematically illustrates a three dimensional perspective view of a system in accordance with a preferred embodiment of the present invention.

For the implantation of the lead 10 in the chosen stimulation site, in accordance with a preferred embodiment of the present invention, a guide catheter 26 with a double curvature is used. With reference to FIG. 2, the guide catheter 26 is illustrated with the lead 10 inserted inside. The distal portion 28 of the guide catheter 26 is open at its end, so as to bring out the distal end of the lead 10 and its anchoring screws 14 by relative axial movement of the lead body 12 inside the guide catheter 26.

In addition, a stylet 30 is inserted inside an inner lumen 32 of the lead 10 so as to stiffen it and straighten the natural curvature of the catheter 26 by more or less axially sliding the stylet 30 within the lead 10.

Figure 3:
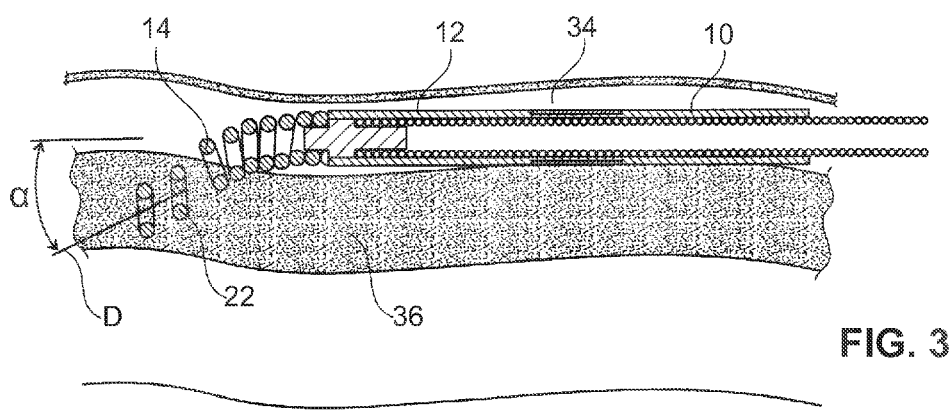
FIG. 3 is a sectional view of the lead of FIG. 1 after it has been implanted in a target vein of the coronary network, with the screw being anchored in the wall of the epicardium.
Figure 4:
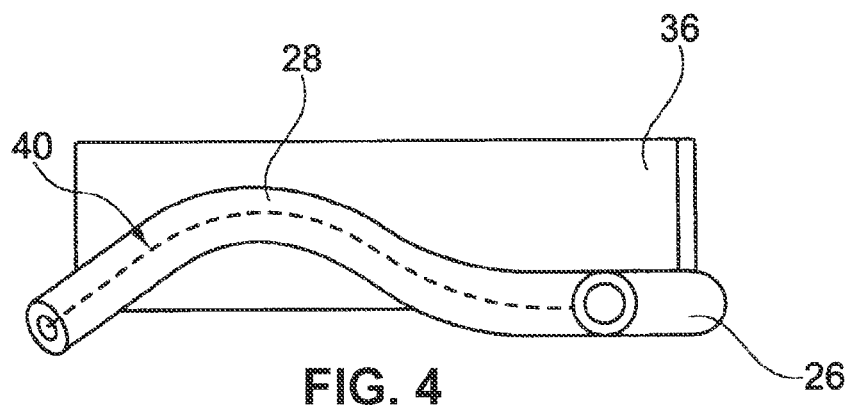
FIG. 4 is an end view according to section AA of FIG. 2.
Figure 5:
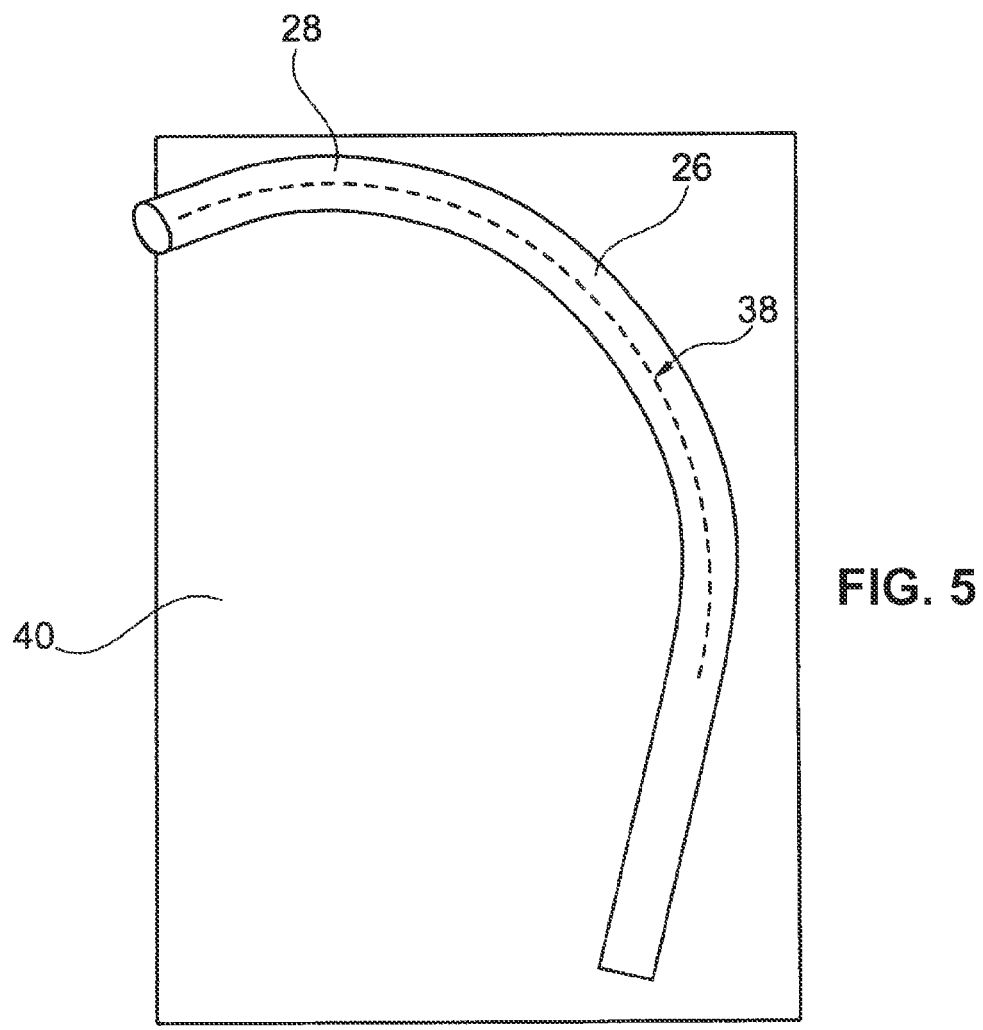
FIG. 5 is a top view according to section BB of FIG. 2.

As indicated above, the catheter 26 has at its distal end 28 a double curvature, each curvature being inscribed in a separate area 38 and 40. The curved surface 38 is an orientation curvature that follows the natural curvature of the coronary veins during the progression of the catheter 26 into the coronary sinus, while the curved surface 40 is a curve for supporting the orientation of the distal portion of the lead 10 once the site of stimulation is reached. More specifically, this supporting curvature 40 has the effect of directing the axis of the anchoring screw 14 not in line with the target vein 34, but instead, as shown in FIG. 3 (after removal of the catheter 26), to the wall facing the epicardium 36 of the target vein. According to this method, the anchoring of the screw 14 and the subsequent screwing of the screw 14 along a direction D makes an angle a with the axial general direction of the lead 10, roughly corresponding to the direction of progression of target vein 34.

The implantation procedure of the screw 14 at the selected site will now be described. This procedure is described in its most complete aspect, but it should be understood by persons of ordinary skill in the art that certain steps or the use of certain elements may be omitted, adapted, or modified without deviating from the scope of the present invention.

According to one embodiment, a technique called OTW (Over-The-Wire) is used. OTW involves introducing into the coronary sinus and then in the coronary network a very thin guide wire provided at its distal end with a flexible termination that is not traumatic. Previously, the practitioner arranges a main catheter to reach the outlet of the coronary sinus, insert the guide wire into the catheter, and pushed into the coronary venous system.

The practitioner inserts the guide catheter 26 according to the invention. The guide catheter 26 may be used as a sub-selection catheter to choose, under fluoroscopy, the path of the venous network that will allow reaching the target vein corresponding to the chosen stimulation site. The self-orientation of the catheter 26 during this phase of positioning results from the principle of least energy, especially during the "left turn" in the area of intersection of the great cardiac vein and a lateral vein.

The self-orientation of the orientation curve locally generates enough torque to force the orientation of the support curvature in the desired position. The predominance of the torque effect of the orientation curvature relatively to the support curvature is related to the fact that, in terms of dimensions:

the radius of curvature of orientation is greater than the support radius curvature, and
the length of the orientation curvature is greater than the support curvature length.

The distance between the area generating the drive torque (orientation curvature) and the area to be controlled (support curvature) is thus extremely limited (a few millimeters).

It should be noted that the present invention requires a single catheter to determine the relative positions of the two curvatures.

Thus, as stated above, the lead solution of the present invention is not operator-dependent: the practitioner just pushes catheter into the target vein for the catheter 26 to self-orient in the desired position after a few beats, frees both hands for the screwing operation, while ensuring a secure and accurate positioning of the screw 14 and holding it in this position during the screwing phase that follows.

According to one embodiment, a hollow dilator catheter is used in the sub-region to establish a gradual transition between the guide wire and the tip of the sub-catheter, particularly to prevent the catheter tip, while sliding on the guide wire, from crashing against the wall of the vein, for example, where a curvature is met at a blocking point in the course of traversing the tortuous vein. This dilator catheter is advantageously preformed in its distal part to facilitate cannulation of the lateral veins. This option allows to compensate the self-positioning of the sub-catheter into the left atrium as it moves into the large vein (because of the principle of least energy, but implemented in the great cardiac vein). This behavior of the dilator catheter enables placement of a left atrial lead even in the proximal part of the great cardiac vein.

Once the desired stimulation site is reached, the practitioner slides the lead 10 inside the catheter 26 until the distal end of the lead 10 and its anchoring screws 14 emerge from the corresponding end of the catheter 26 (configuration illustrated in FIG. 2). Because of the double curvature described above, the distal end of catheter 26, the distal orifice of the catheter 26 is directed toward the epicardium 36 making an angle a compared to the general direction of the target vein. The catheter 26 is introduced into the lead 10 until it emerges from the catheter housing and its anchoring screw 14 comes in contact with the epicardium. An initial mapping is conducted to electrically test the contact point(s) and validate the chosen stimulation site. If the position is not satisfactory, the practitioner moves the catheter along the vein and test a new site until a suitable location is found.

The final anchoring is obtained by imparting an axial rotation to the lead body in the case of a fixed screw lead. For a pin-driven lead, the axial rotation is imparted to the connector plug, where at the proximal side the connection plug is secured to a conductor extending axially within the lead body. The surgeon holds in one hand the proximal end of the lead body and turns a pin at the proximal end with the other hand, directly or through the intermediary of a tool. The pin is secured to an axial conductor extending within the lead body, and this conductor is free in rotation and is connected at its distal end to the connector plug deployment mechanism of the screw. Another possibility is to introduce a specific screwing stylet into the lumen 32 of the lead body, especially in case when the sheath does not have a sufficient torsional rigidity to drive the screw directly from the proximal end.

In an alternative embodiment, a retractable screw is used instead of a fixed screw. In this case, the rotation first deploys the screw out of its slot and subsequently penetrates the screw into the wall of the epicardium.

After the screw 14 is anchored into the wall of epicardium, the catheter 26 is removed. The removal of the catheter 26 is performed according to a standard procedure of cutting through a slitter tool, as described, for example in, EP 2039390 A1 and its US counterpart U.S. Published Application 2009/0071012 (Sorin CRM S.A.S. formerly known as ELA Medical).

The final and definitive installed configuration is illustrated in FIG. 3.

Advantages of using the present invention include the following improvements over the prior known coronary venous leads:
  the quality of the fixation for anchoring screws;
  the stability of the electrical contact with the tissue regardless of the size of the vein;
  the ability to map large portions of the vein before the final fixation;
  the possibility to expand the exploitable part of the vein, particularly towards the proximal part of the venous system, known to be the least exposed to the risk of phrenic nerve stimulation, but having with traditional leads, the disadvantage of a lower stability due to a larger diameter;
  the concentration of the electrical stimulation in a deep region of the epicardium, decreasing the risk of phrenic nerve stimulation;
  the improved extraction capacity, by a simple unscrewing of the distal end;
  the mechanical simplicity of the system, a low manufacturing cost and a high reliability.

One skilled in the art will appreciate that the present invention can be practiced by other than the embodiments disclosed herein, which are provided for purposes of illustration and not of limitation.

I claim:

1. A system implantable in a coronary venous system, for stimulating a left heart chamber by a generator of an active implantable medical device, comprising:
  a stimulation lead having a distal end, a proximal end and a lead body having a sheath of a deformable material, said stimulation lead having a lead head at the distal end, with at least one stimulation electrode adapted to come into contact with a region facing an epicardial wall of a target vein of a patient's coronary network, and said stimulation lead having at the proximal end means for coupling to a generator of the active implantable medical device, and
  a removable guide catheter comprising a hollow tube having a proximal end and a distal end, both ends being open and having a lumen for receiving the stimulation lead for movement translationally within the guide catheter between a retracted position and a deployed position, at the retracted position the lead head being positioned at a guide catheter lumen distal end, and at the deployed position the lead head with the at least one stimulation electrode extending from said catheter lumen distal end,
  wherein the hollow tube of the guide catheter is elastically deformable and relatively more rigid than the sheath of the lead body,
  wherein the stimulation lead is a screw lead, having an anchoring screw axially extending along the lead head configured to penetrate the patient's epicardial tissue in response to a screw motion imparted to the lead head;
  wherein the sheath of the lead body is not pre-shaped at the distal end of the stimulation lead, and wherein the hollow tube of the guide catheter is a single pre-shaped tube with, in absence of a stress, first and second curvatures inscribed in two separate surfaces, said first and second curvatures self-orienting the distal end of the guide catheter tube in the target vein with the lead head in the retracted position, and configured to maintain an axis of the anchoring screw towards the epicardial wall of the target vein during a combined motion of screwing and moving the lead head to the deployed position
  wherein the anchoring screw comprises an end portion that is configured to penetrate the patient's epicardial tissue and a tip active electrically conductive region extending through an electrically isolated intermediary part.

2. The system of claim 1, wherein an axial length of the tip active electrically conductive region is at most 1 mm.

3. The system of claim 1, wherein the two separate surfaces defining the first and second curvatures comprise a first surface corresponding to the first curvature defined by an orientation of the pre-shaped guide catheter tube and a second surface corresponding to the second curvature defined by a naturally bent shape of the distal end of the guide catheter tube.

4. The system of claim 1, wherein the anchoring screw is a screw extending axially from the lead head.

5. The system of claim 1, further comprising a housing wherein the anchoring screw is a movable screw, retractably mounted in the housing.

6. The system of claim 1, wherein the anchoring screw of the stimulation lead forms said at least one stimulation electrode.

7. The system of claim 1, wherein the sheath of the lead body has a torsional rigidity sufficient to transmit a rotating movement from the proximal end of the lead to screw the anchoring screw.

8. The system of claim 7, wherein the sheath of the lead body further comprises a slot to rotate the anchoring screw, and wherein the system further comprises:
  a removable stylet, for inserting into said slot and moving in translation within the lumen up to the lead head, said stylet having means for coupling in rotation with the lead head, said stylet having a length and a torsional rigidity sufficient to transmit a rotation movement over the length of the stylet up to the means of coupling from a proximal end of the stylet to screw the anchoring screw.

9. The system of claim 1, wherein the diameter of the lead body is less than or equal to 5 French.

10. The system of claim 1, wherein the anchoring screw comprises a helical end portion that is configured to penetrate the patient's epicardial tissue and is connected to the lead head by a transition portion, wherein the transition portion is mechanically deformable in flexion.

11. The system of claim 10, wherein the transition portion is part of the helical end portion of the anchoring screw having adjacent turns.

12. The system of claim 1, further comprising:
a removable guide wire, the guide wire configured to, after introduction into the coronary venous system to the target vein, receive the guide catheter and guide the system up to the target vein.

13. The system of claim 1, wherein said guide catheter is a sub-selection catheter for vein selection, and further comprising:
a main guide catheter comprising a hollow tube open at both ends with a lumen, wherein the sub-selection catheter is introduced and moved in translation and rotation within the main guide catheter for progression in the coronary venous system to reach the target vein.

14. An implantable system for stimulating a left heart chamber, comprising:
a stimulation lead comprising a sheath of a deformable material, a lead head at a distal end, at least one stimulation electrode adapted to come into contact with an epicardial wall, and a coupling mechanism at a proximal end for coupling to a generator of an active implantable medical device, and
a removable guide catheter having an open proximal end, an open distal end, and a lumen between the open proximal end and the open distal end for receiving the stimulation lead for movement translationally within the guide catheter, wherein the hollow tube of the guide catheter is elastically deformable and relatively more rigid than the sheath of the lead body,
wherein the stimulation lead is a screw lead, having an anchoring screw configured to penetrate the patient's epicardial tissue in response to a screw motion imparted to the lead head, wherein the anchoring screw comprises an end portion that is configured to penetrate the patient's epicardial tissue and an electrically conductive tip having an active region extending through an electrically insulated region;
wherein the sheath of the lead body is not pre-shaped, and
wherein the guide catheter is a single pre-shaped tube with, in the absence of a stress, first and second curvatures inscribed in two separate surfaces, said first and second curvatures self-orienting the distal end of the guide catheter tube.

15. The system of claim 14, wherein the stimulation lead moves translationally with the guide catheter between a retracted position and a deployed position.

16. The system of claim 15, wherein in the retracted position, the lead head is positioned at the distal end of the guide catheter, and in the deployed position, the lead head extends from said distal end of the guide catheter.

17. The system of claim 16, wherein in the first and second curvatures are configured to maintain the axis of the anchoring screw towards the epicardial wall during a combined motion of screwing and moving the lead head to a deployed position.

18. The system of claim 14, wherein the anchoring screw extends axially from the lead head.

19. The system of claim 14, wherein the sheath is not pre-shaped at the distal end of the stimulation lead.

20. The system of claim 14, wherein the anchoring screw comprises a helical end portion that is configured to penetrate the patient's epicardial tissue and is connected to the lead head by a mechanically deformable transition portion.

* * * * *